(12) United States Patent
Winsor

(10) Patent No.: US 8,814,849 B1
(45) Date of Patent: Aug. 26, 2014

(54) INFUSION CHECK VALVE FOR MEDICAL DEVICES

(71) Applicant: Nexus Medical, LLC, Lenexa, KS (US)

(72) Inventor: Chris Winsor, Overland Park, KS (US)

(73) Assignee: Nexus Medical, LLC, Lenexa, KS (US)

( * ) Notice: Subject to any disclaimer, the term of this patent is extended or adjusted under 35 U.S.C. 154(b) by 0 days.

(21) Appl. No.: 13/767,587

(22) Filed: Feb. 14, 2013

(51) Int. Cl.
A61M 25/18 (2006.01)

(52) U.S. Cl.
USPC ........... 604/537; 604/523; 604/533; 604/534; 604/535; 604/536; 604/538; 604/539; 604/284

(58) Field of Classification Search
USPC ......... 604/523, 533, 534, 535, 536, 537, 538, 604/539, 284
See application file for complete search history.

(56) References Cited

U.S. PATENT DOCUMENTS

| | | | |
|---|---|---|---|
| 7,140,592 B2 * | 11/2006 | Phillips | 251/149.6 |
| 7,350,764 B2 * | 4/2008 | Raybuck | 251/149.1 |
| 7,645,274 B2 * | 1/2010 | Whitley | 604/537 |
| 7,959,614 B2 | 6/2011 | Dikeman et al. | |
| 7,967,797 B2 | 6/2011 | Winsor et al. | |
| 8,177,760 B2 * | 5/2012 | Rome et al. | 604/247 |
| 8,414,542 B2 * | 4/2013 | Stroup | 604/246 |
| 8,454,579 B2 * | 6/2013 | Fangrow, Jr. | 604/539 |
| 2005/0087715 A1 * | 4/2005 | Doyle | 251/149.1 |
| 2011/0015580 A1 * | 1/2011 | Stroup | 604/207 |

* cited by examiner

Primary Examiner — Scott Medway
(74) Attorney, Agent, or Firm — Erise IP, P.A.

(57) ABSTRACT

An intravascular valve assembly having a valve case and a flexible pressure-actuated flow control valve. The valve case includes attached proximal and distal case portions that present respective spaced apart fluid ports and a fluid passageway extending between the ports. The flexible pressure-actuated flow control valve is disposed within the fluid passageway and includes a slitted central valve wall. The proximal case portion includes an axially-extending boss that projects distally, with a portion of a distal end of the boss contacting the flow control valve. The valve permits fluid flowing in a distal direction to pass through the slit. Fluid flowing in a proximal direction, however, causes the valve to compresses against the boss and the slit to close, thus restricting fluid flow in a proximal direction.

14 Claims, 15 Drawing Sheets

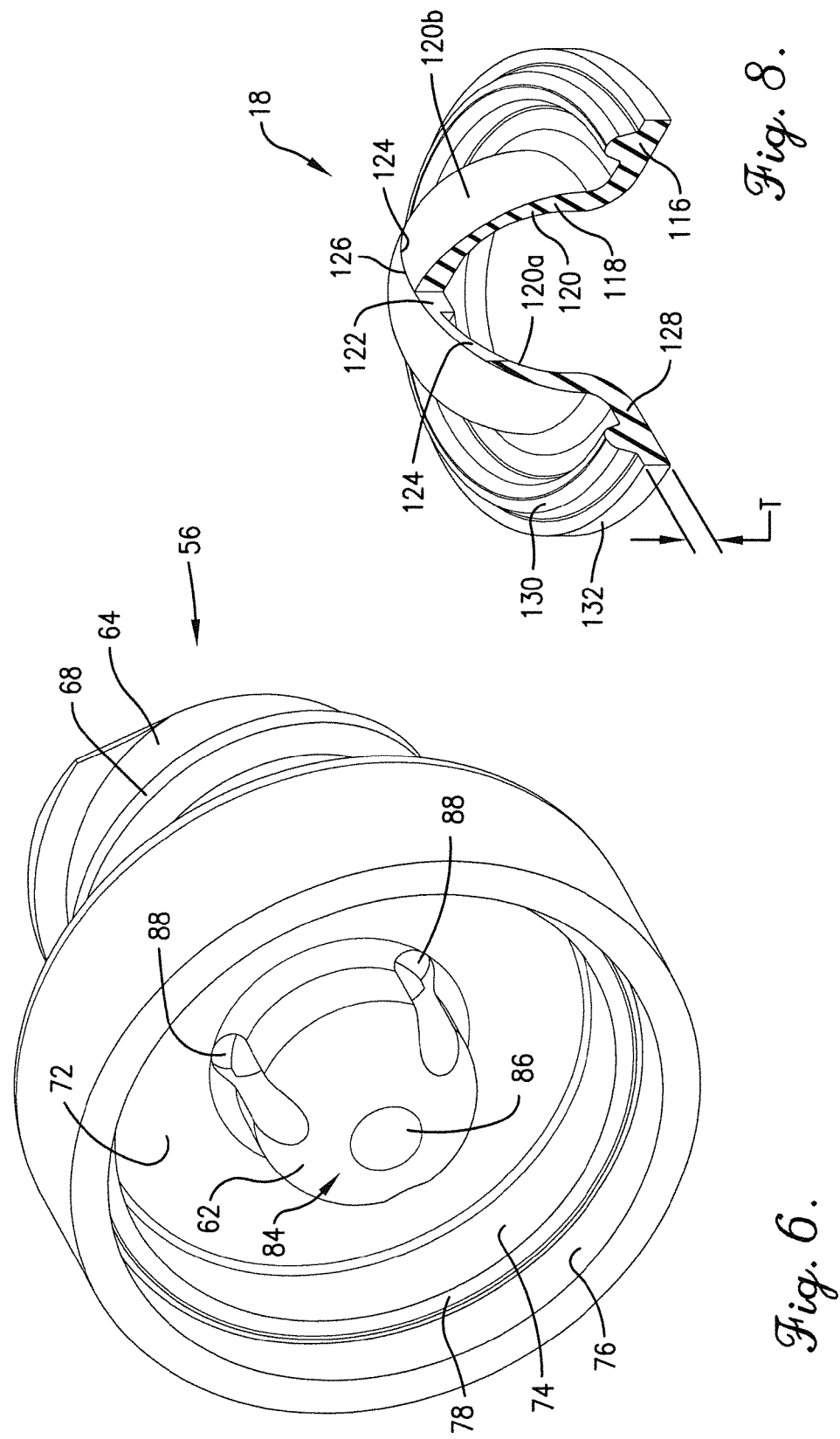

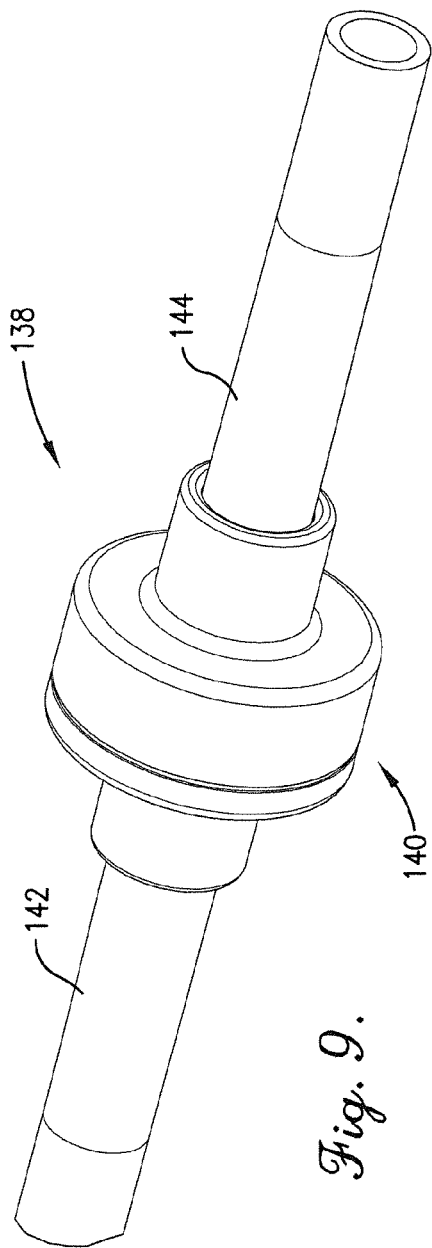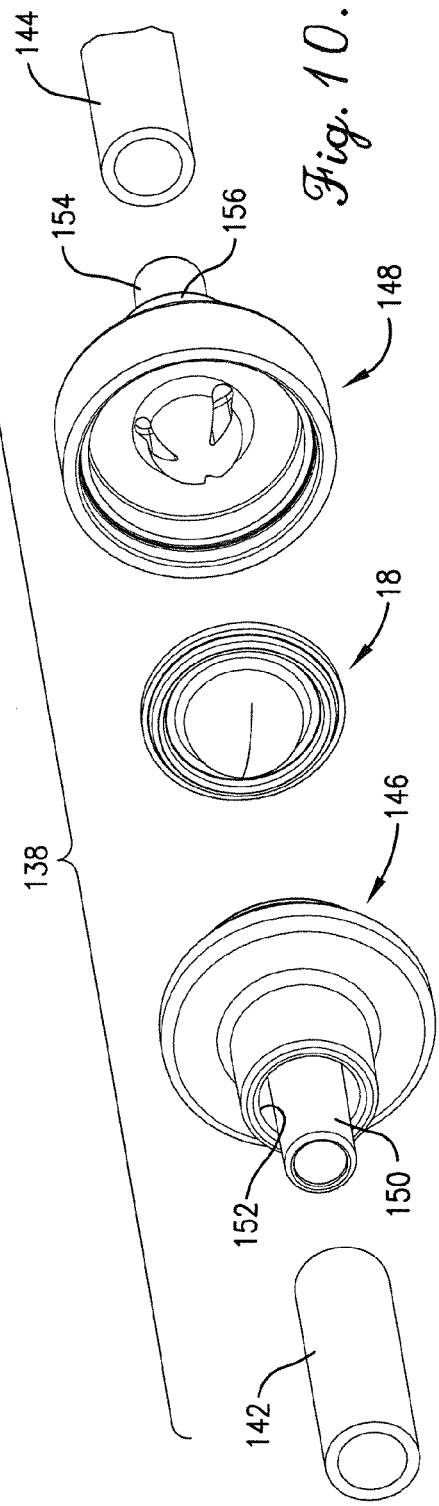

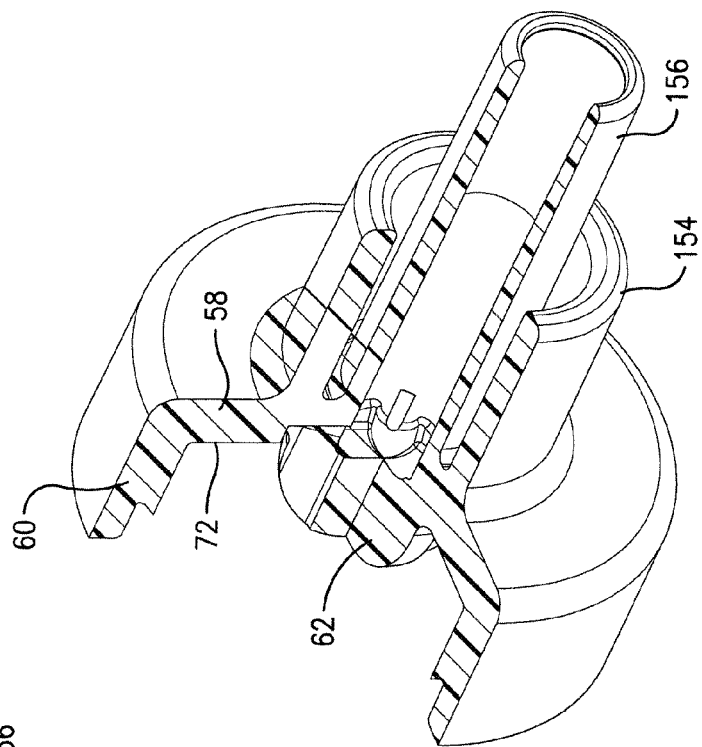
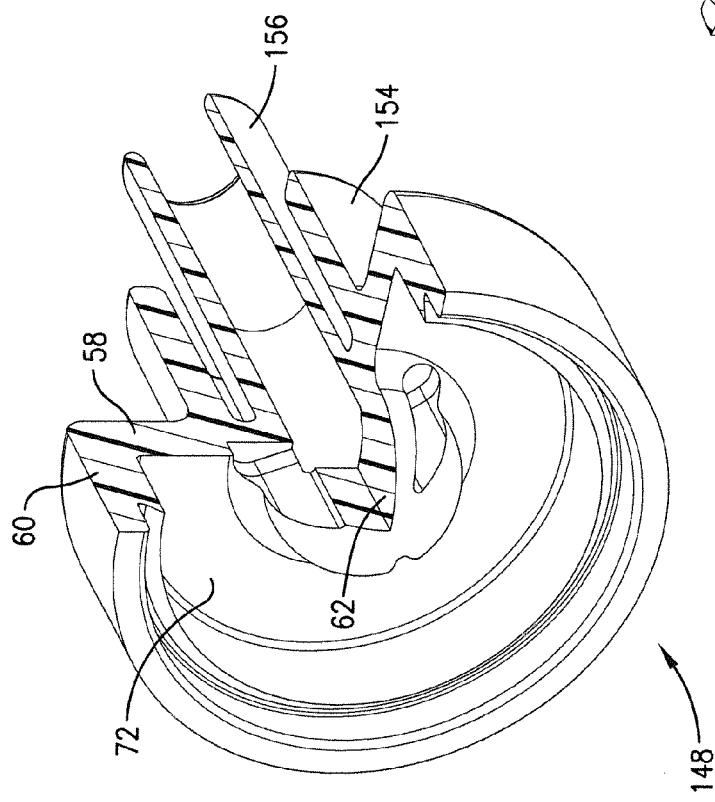

US 8,814,849 B1

INFUSION CHECK VALVE FOR MEDICAL DEVICES

BACKGROUND

1. Field

The present invention relates generally to infusion devices used for the administration of various fluids and medications to patients. More specifically, embodiments of the present invention are directed to an infusion check valve assembly for an intravenous catheter.

2. Related Art

The use of intravenous devices for the administration of parenteral and other fluids to patients is a common practice. A variety of devices for such purposes have been proposed in the past, such as a simple length of tubing having a fitting on one end for making connection with a source of fluid (e.g., a bottle or flexible bag), while the other end is provided with a needle or catheter that may be inserted into the vein of a patient. A persistent problem with prior infusion devices is referred to as fluid reflux, or the tendency for fluids, such as blood or medication, to be drawn into the infusion apparatus. Fluid reflux can occur in prior art devices, for example, when a gravity supply fluid source is empty, when medication is infused through an adjacent component, or when a cannula is removed from a septum or port.

Prior art pressure-activated infusion devices that reduce fluid reflux using a flexible valve are problematic due to design and manufacture-related issues. Flexible valves may often times mechanically invert within the internal passage of the valve housing due to elevated back pressure. Upon such an inversion, the flexible valves may be forced into a permanently open position, thus permitting blood or other unwanted fluids and medication to reflux back through the valve. Prior art check valves, such as certain types of disc valves, used to reduce or restrict fluid reflux typically require high cracking pressures for incoming fluids to open and pass through the valves. In certain applications, high cracking pressures may be acceptable. However, in other applications, lower cracking pressures may be necessary. To reduce the cracking pressures in prior art check valves, the valves are often designed with large diameters, such that the valves present enough surface area to reduce the cracking pressures to acceptable levels. Although such prior art check valves may assist in reducing fluid reflux, because of the increased size of the valves, they may be inefficient, and often times impractical, for the intravenous administering of fluid and medication.

There is accordingly a need in the art for improved intravascular devices equipped with a check valve component that eliminates the possibility of fluid reflux, while providing for the efficient administration of medical fluids.

SUMMARY

Embodiments of the present invention are directed to an intravascular check valve assembly that restricts fluid reflux in a proximal direction, while maintaining a low cracking pressure for fluids to be introduced through the assembly in a distal direction.

An aspect of the present invention concerns an intravascular check valve assembly that controls fluid flow in distal and proximal directions. The assembly broadly includes a valve case and a flexible pressure-actuated flow control valve. The valve case includes attached proximal and distal case portions, with the distal case portion positioned closer to a patient when the device is in use and a proximal case portion opposite and extending away from the distal case portion. The case portions present respective spaced apart fluid ports and a fluid passageway extending between the ports. The flexible pressure-actuated flow control valve is disposed along the fluid passageway to control fluid flow therethrough. The valve includes a central valve wall having at least one slit at a distal end of the wall, with the wall presenting distal-facing and proximal-facing surfaces. The proximal case portion of the valve case includes an axially-extending boss that distally projects from the proximal case. The boss includes a portion of a distal end that engages at least a portion of the proximal-facing surface of the flow control valve. The boss includes one or more channels positioned adjacent to a radial-most edge of the boss, such that the channels fluidly connect the fluid port of the proximal case to the proximal-facing surface of the flow control valve. The valve wall flexes to open the at least one slit in response to a fluid flowing in a distal direction through the channels of the boss and through the valve. The valve wall compresses against the boss and closes the slit in response to a fluid flowing in a proximal direction, thereby preventing fluid flow through the valve assembly in the proximal direction.

Other aspects and advantages of the present invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein:

FIG. 6 is a distal perspective of a valve support with an axially extending boss, showing the axially-extending boss with a distal facing flat surface on the boss's distal end.

FIG. 8 is a distal perspective of the flow control valve shown in FIGS. 2-3, showing the flow control valve cross-sectioned to depict a slit central valve wall and an annular flange surrounding the central valve wall, and further showing a radially extending wall of the flange and an endless annular projection extending distally from the flange wall.

FIG. 9 is a perspective view of an inline check valve system embodiment of the present invention, including an inline check valve assembly.

FIG. 10 is an exploded distal perspective view of the inline check valve system shown in FIG. 9, including the inline check valve assembly and particularly showing tubular members, a slip luer fitting, a flow control valve, and a slip luer valve support.

FIG. 11 is a distal perspective of the slip luer valve support shown in FIGS. 9-10, showing the slip luer valve support cross-sectioned to depict a hub and a cup-like structure that includes a valve seat, a sidewall, and an axially-extending boss.

FIG. 12 is a proximal perspective of the slip luer valve support shown in FIGS. 9-10, showing the slip luer valve support cross-sectioned to depict a hub and a cup-like structure that includes a valve seat, a sidewall, and an axially-extending boss.

Figure 1:
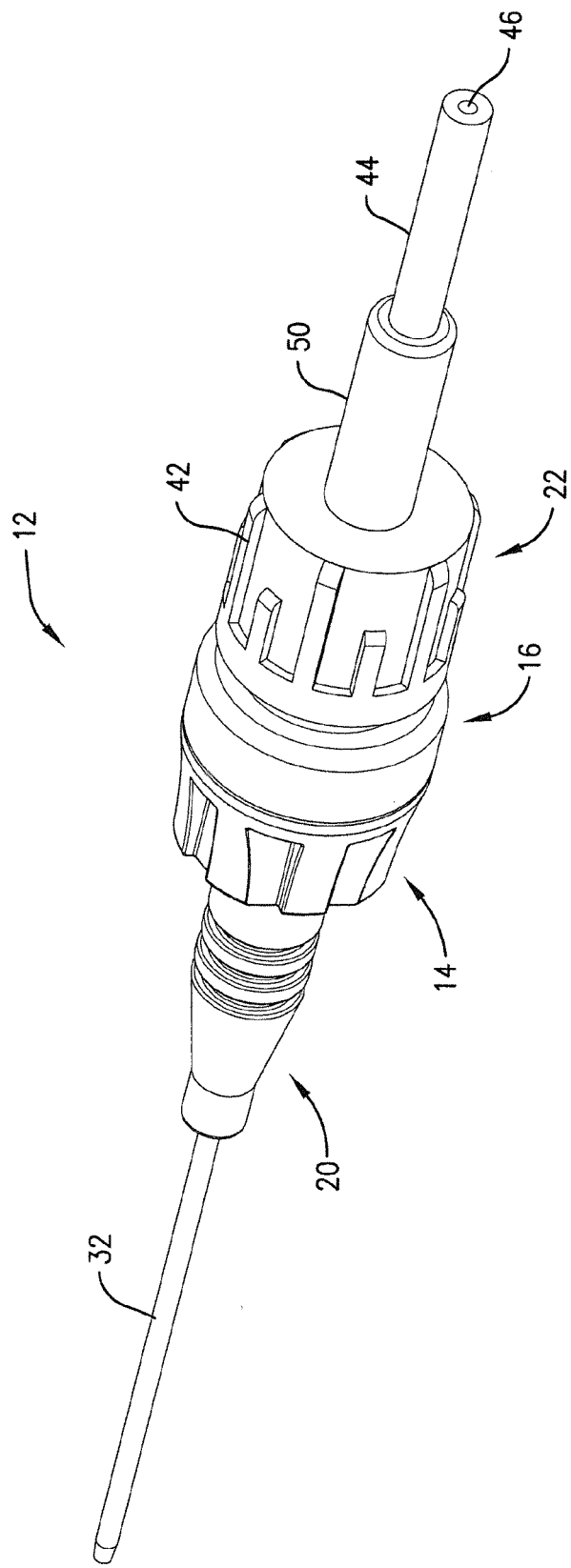
FIG. 1 is a perspective view of an intravascular check valve assembly constructed in accordance with embodiments of the present invention.

The drawing figures do not limit the present invention to the specific embodiments disclosed and described herein. The drawings are not necessarily to scale, emphasis instead being placed on clearly illustrating the principles of the invention.

DETAILED DESCRIPTION

Figure 2:
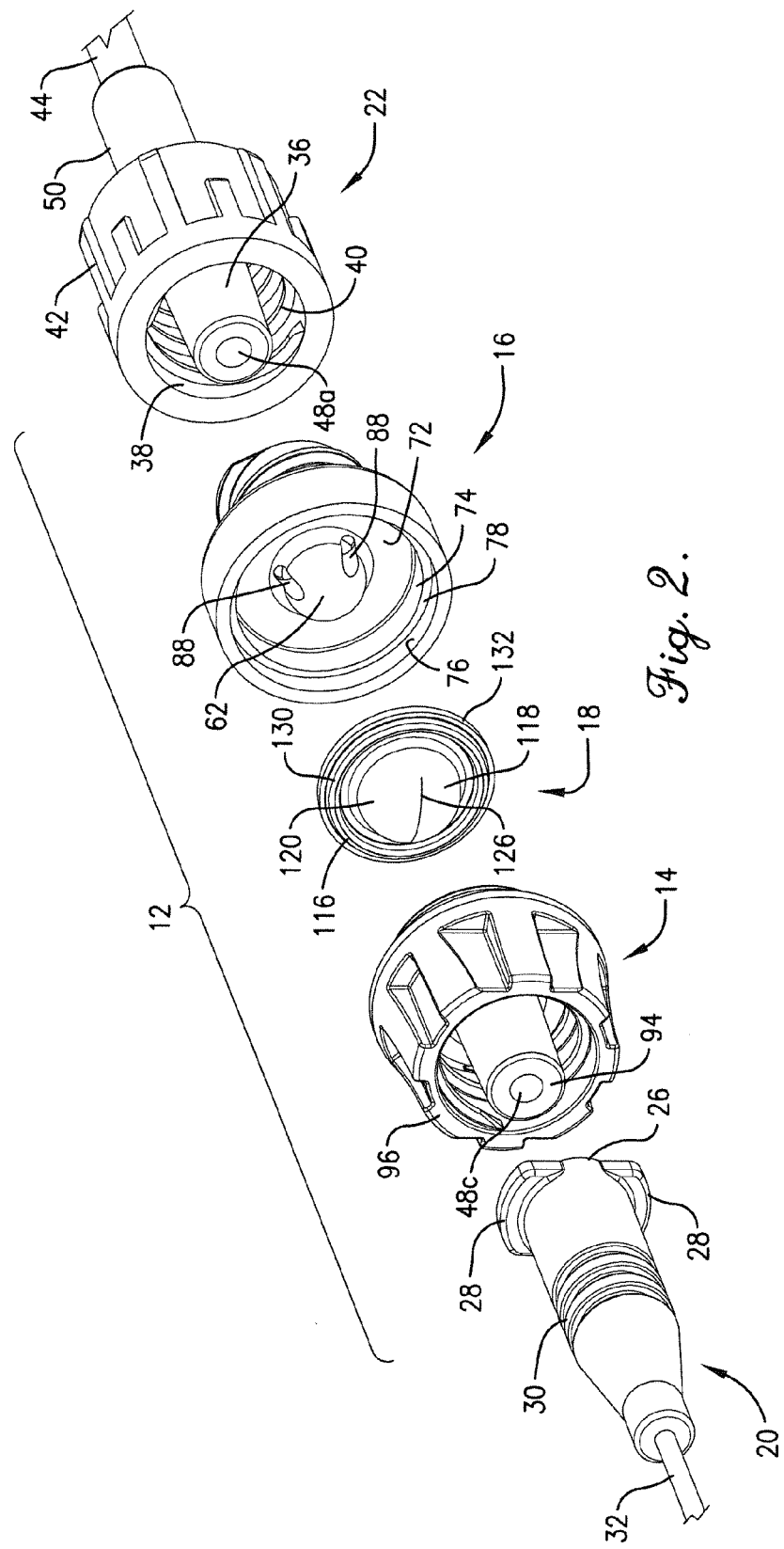
FIG. 2 is an exploded distal perspective view of the check valve assembly shown in FIG. 1, particularly showing a peripheral catheter, a luer lock fitting, a flow control valve, a valve support, and a support body.
Figure 3:
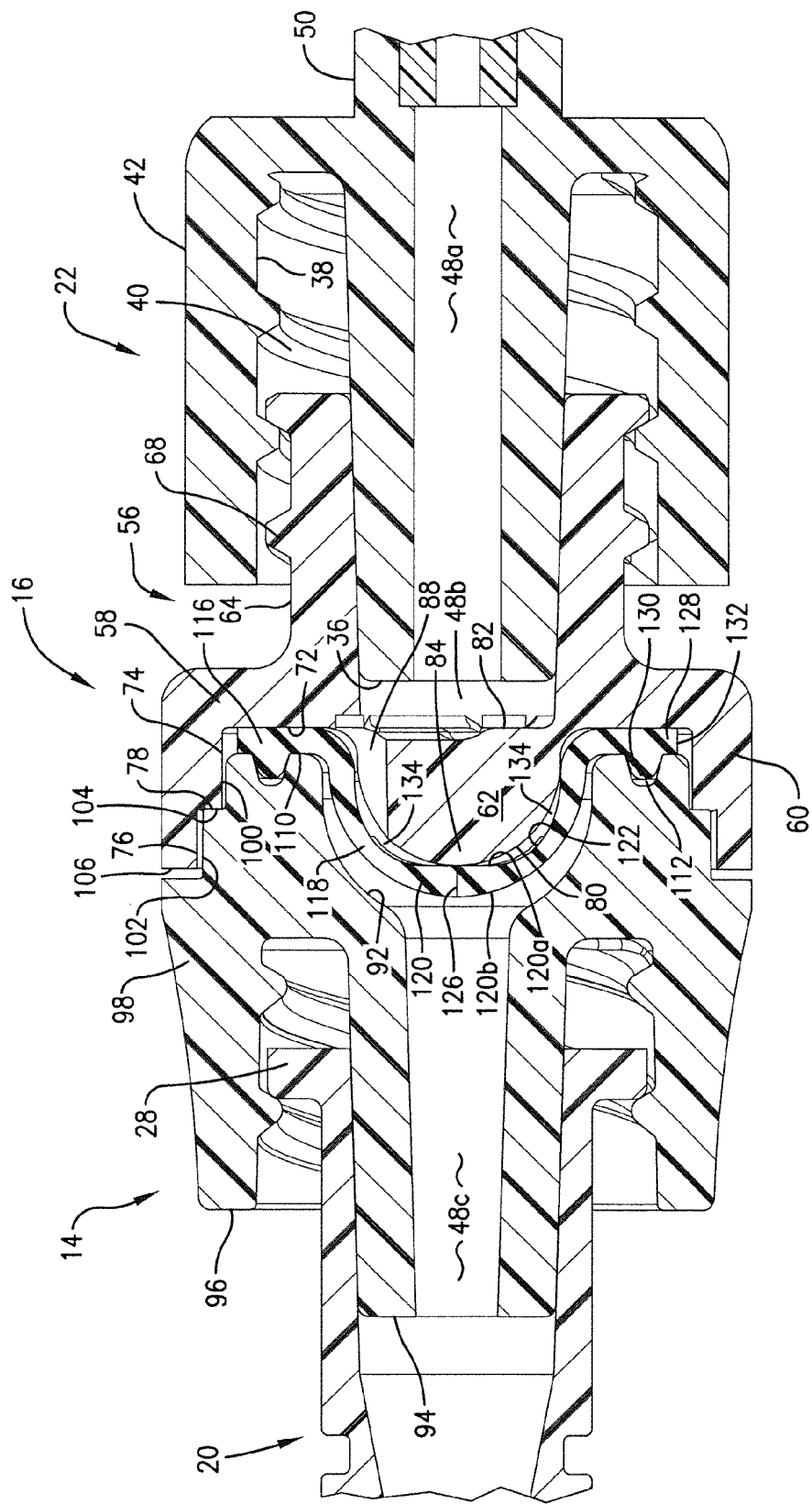
FIG. 3 is a cross section of the check valve assembly shown in FIGS. 1-2, showing the peripheral catheter, the luer lock fitting, the flow control valve, the valve support, and the support body.

Beginning with FIGS. 1-3, a valve assembly 12 is generally comprised of a luer lock fitting 14 positioned on a distal end of the valve assembly, and a valve support 16 attached to a proximal end of the luer lock fitting 14 and operable to receive a flexible pressure-actuated flow control valve 18. The valve assembly 12 may be installed in line between a peripheral catheter 20 positioned on the distal end of the luer lock fitting 14 and a support body 22 removably connected to a proximal end of the valve support 16. Although the valve assembly is shown with the peripheral catheter 20 and support body 22, it will be appreciated that the valve assembly can be used in other applications. For example, the valve assembly 12 could be used with a central venous catheter (CVC), another intravascular catheter, or a needle. Furthermore, the valve assembly could be used with other types of connection components, tubing, etc. As used herein, the terms "distal" and "proximal" refer, respectively, to directions toward and away from a patient.

In more detail, the illustrated peripheral catheter 20 is itself entirely conventional and includes an annular proximal base 26 with diametrically opposed connection tabs 28 for threaded connection to the luer lock fitting 14. The catheter 20 also includes a distally extending barrel 30 and cannula 32 secured to the distal end of the barrel 30. As is customary, the cannula 32 is inserted into a patient so that medicaments can be injected via the valve assembly 12. As previously mentioned, the principles of the present invention are equally applicable to other catheter designs, as well as other components permanently or removably secured to the valve assembly.

The support body 22 has a generally cylindrical overall shape and may be a unitary body molded from a thermoplastic, synthetic resin, or the like. The support body 22 includes a distal annular inner barrel 36, and a distal annular outer connection wall 38. The outer connection wall 38 includes a threaded interior surface 40 and an exterior surface 42 that is swaged or flanged to facilitate gripping. The support body 22 is otherwise hollow at its distal end, such that it can receive the valve support 16, which may be secured to the support body 22 between the inner barrel 36 and the threaded interior surface 40. The proximal end of the support body 22 is axially apertured to permit coupling with a supply tube 44 having an outer surface and an inner surface defining a lumen 46. The inner barrel 36 presents a fluid passageway 48a that is fluidly connected with the lumen 46. The proximal end of the support body 22 is equipped with a molded fitment 50 to accommodate the supply tube 44. The proximal end of the supply tube 44 is coupled with a fluid reservoir (not shown) so that the lumen 46 is in fluidic communication with the reservoir.

Although not shown in FIGS. 1-3, the support body 22 may also be equipped with a stopcock or a plurality of infusion ports with plugs for receiving a syringe and/or needle. A pump may be installed in line with the supply tube 44, which may also be equipped with clamps (neither is shown).

The catheter 20 and supply tube 44 are flexible and pliant to facilitate placement and usage and to minimize both mechanical insult to the blood vessels and patient discomfort during long-term use. They may be constructed of any suitable medical grade material, such as, for example, polyethylene, polyvinyl chloride, Teflon, silicone elastomer or polyurethane or mixtures thereof. The material may be coated or impregnated with an antimicrobial or antiseptic composition to reduce bacterial adherence and biofilm formation. The catheter 20 may also be constructed of a radiopaque material in order to facilitate imaging for locating any breaks and/or separated sections.

The valve support 16 serves to support and interconnect the support body 22 and luer lock fitting 14. The valve support 16 preferably comprises a molded synthetic resin rigid body that includes a hub 56 and a cup-like structure that includes a valve seat 58, a sidewall 60, and an axially-extending boss 62 that projects distally from the valve seat 58. The hub 56 has a hollow, cylindrical configuration, including a proximal neck 64 with a fluid passageway 48b. The neck 64 includes a series of luer lock threads 68 designed for mating engagement with corresponding standard luer threads in the support body 22. Alternately, a conventional threaded or bayonet-type fitting may be substituted in the neck 64 and support body for the luer fittings shown and described. The fluid passageway 48b extends through the hub and the mid-section and is operable to receive the inner barrel 36 from the support body 22. Certain embodiments may provide for the passageway 48b to have a diameter that ranges from about 0.070 inches to about 0.125 inches. The passageway 48b serves as the fluid connection between the inner barrel 36 and the cup-like structure that holds the flow control valve 18. However, it is also within the scope of the present invention to have additional or alternative structure provided to interconnect the cup-like structure and the hub.

Remaining with FIGS. 1-3, the cup-like structure is configured to hold the flow control valve 18, as will be discussed further. The valve seat 58 comprises a radially-extending wall attached to the distal end of the hub 56 and presents a proximal flange-engaging face 72. The sidewall 60 comprises an annular wall that presents interior, annular, proximal and distal axial surfaces 74,76 that are joined by a shoulder 78. The sidewall 60 extends endlessly about the valve seat 58 and is preferably integrally formed with the valve seat.

Figure 5:
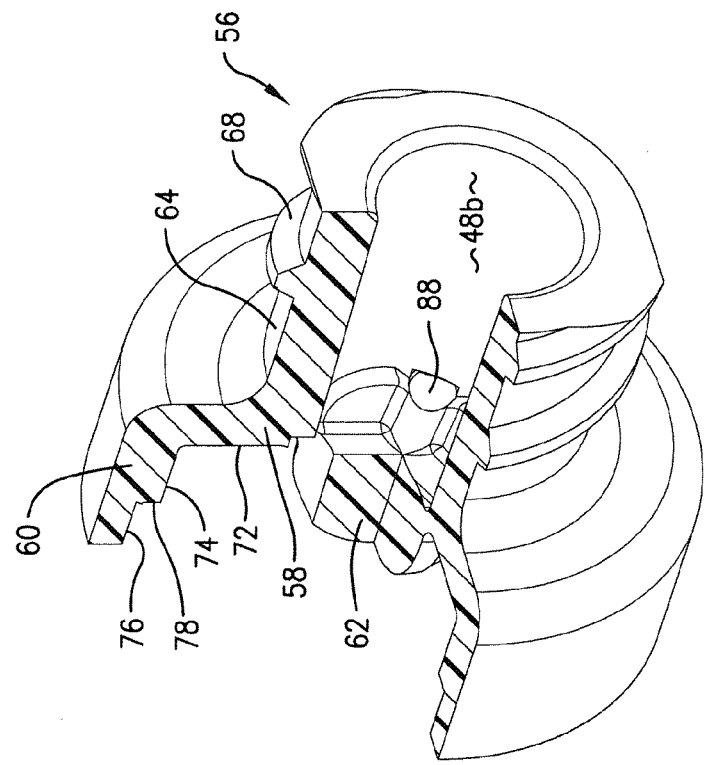
FIG. 5 is a proximal perspective of the valve support shown in FIGS. 1-4, showing the valve support cross-sectioned to depict the hub and the cup-like structure that includes the valve seat, the sidewall, and the axially-extending boss.
Figure 4:
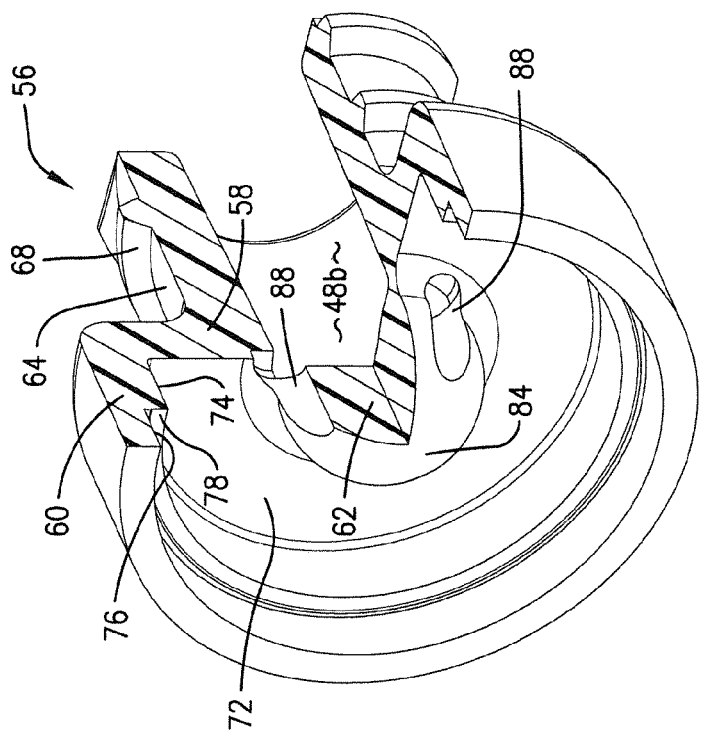
FIG. 4 is a distal perspective of the valve support shown in FIGS. 1-3, showing the valve support cross-sectioned to depict a hub and a cup-like structure that includes a valve seat, a sidewall, and an axially-extending boss.

As best illustrated in FIGS. 3-5, the axially-extending boss 62 projects distally from the valve seat 58 and, in certain embodiments, presents a distal-facing surface 80. The boss 62 includes a proximal base that presents a proximally-facing radial surface 82 extending across an entire radial width of the fluid passageway 48b. In certain embodiments, such as illustrated in FIG. 3, the distal-facing surface 80 may be arcuate-shaped. In other embodiments, the distal-facing surface 80 may be substantially arcuate-shaped, such as hemispherical or parabolical. In still other embodiments, the distal-facing surface 80 may include various other shapes, such as conical, cylindrical, rectangular, square, or the like. In even further embodiments, the boss 62 may be complementary-shaped with a shape of at least portions of the valve 18, as will be discussed in more detail below. The following descriptions of the relative positioning between the valve 18 and boss 62 are applicable when the valve is in a natural or an at rest state (i.e., fluid is not flowing in either a proximal or distal direction through the valve assembly 12). As illustrated in FIG. 3, the boss extends axially, such that at least a portion of a distal end 84 of the boss 62 may contact at least a portion of the valve 18, with the distal end 84 generally comprising the distal most axial one-third of the boss 62. In certain embodiments, a distal most portion of the distal end 84, including an apex of the boss 64, contacts a portion of the valve 18. However, in other embodiments, portions of the distal end 84 other than the distal most portion may contact the valve 18. In even further embodiments, the boss 62 may not contact the valve 18 but may be separated from the valve by at least some nominal distance. Embodiments of the present invention contemplate various contact and separation arrangements between the boss 62 and the valve 18, so long as the boss 62 and valve 18 are operable to restrict the flow of fluid in a proximal direction, as will be discussed in more detail below.

Figure 7:
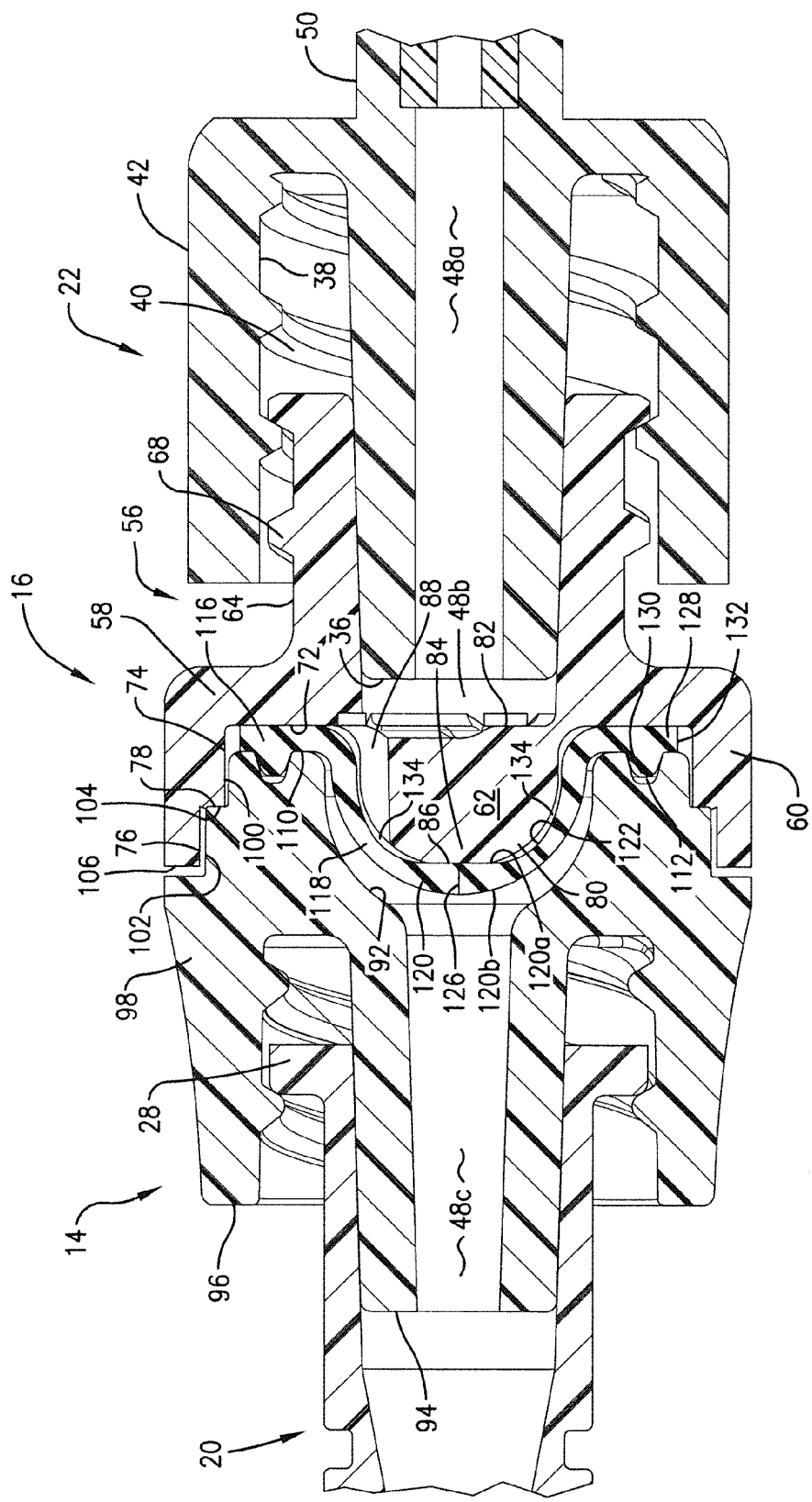
FIG. 7 is a cross section of a check valve assembly with the valve support shown in FIG. 6, including the axially-extending boss with the distal facing flat surface, with the cross section showing the peripheral catheter, the luer lock fitting, the flow control valve, the valve support, and the support body.
Figure 13:
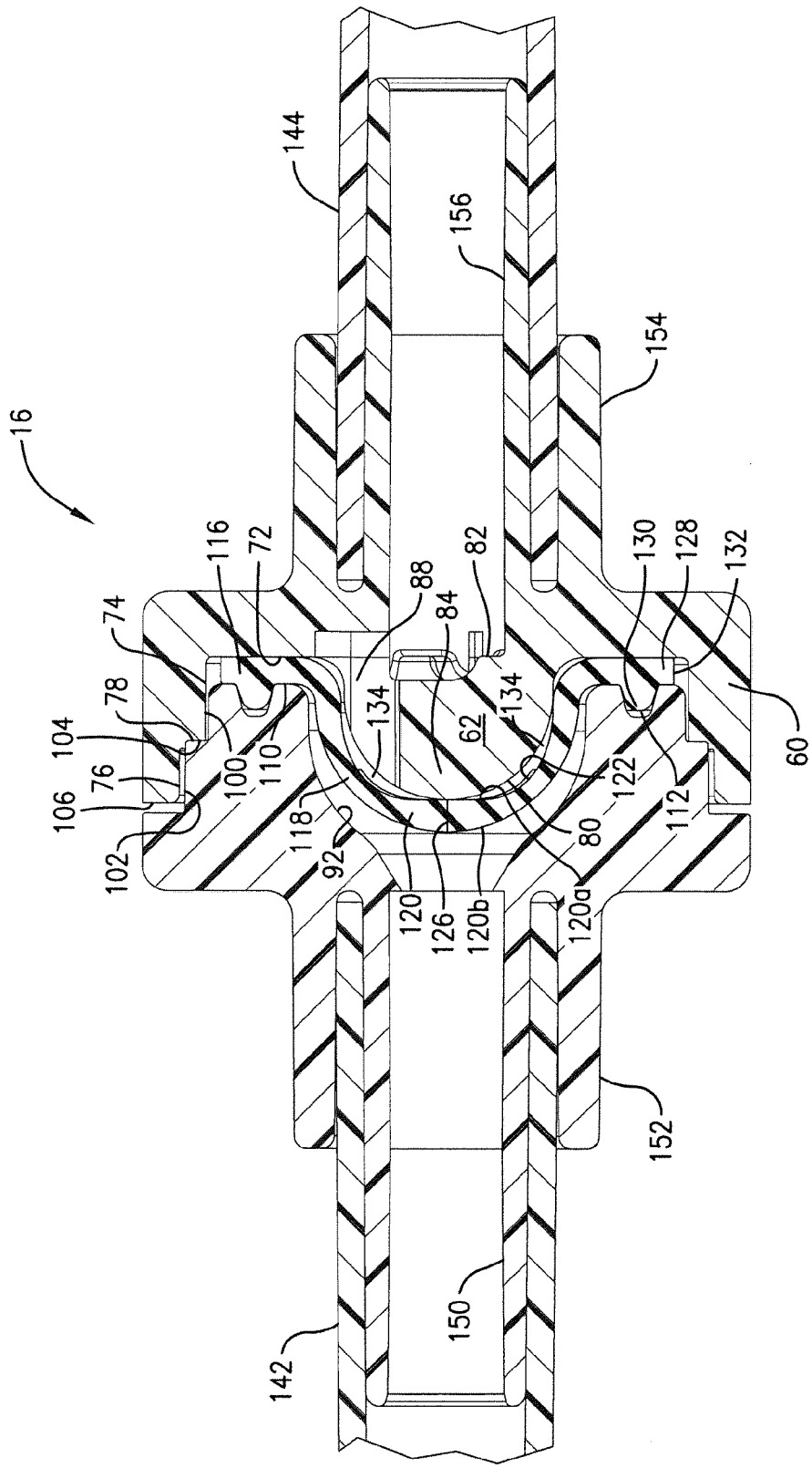
FIG. 13 is a cross section of the inline check valve system shown in FIGS. 9-10, including the inline check valve assembly and particularly showing tubular members, a slip luer fitting, a flow control valve, and a slip luer valve support.

In further embodiments, the distal end 84 of the boss 62 may include a distal facing flat surface 86 (see FIGS. 6-7) comprising a plurality of points each lying within a plane that extends entirely radially with respect to the valve assembly 12. In such an embodiment and as illustrated in FIG. 7, the flat surface 86 may contact at least a portion of the valve 18. However, as described above, embodiments of the present invention include various contact and separation arrangements between the boss 62 and the valve 18, so long as the boss 62 and valve 18 are operable to restrict the flow of fluid in a proximal direction, as will be discussed in more detail below.

Returning now to FIGS. 3-5, the boss 62 is generally solid; however, the boss includes at least one generally axial directed channel 88 that provides a flow through opening, such that the channel 88 fluidly communicates with the fluid passageway 48b. The at least one channel is generally positioned axially through the boss 62, presenting a proximal opening in the proximally-facing radial surface 82 and a distal opening in the distal-facing surface 80. Because the distal opening of the channel is presented in the distal-facing surface 80 of the boss 62, the distal opening is presented in the form of a cutout on the surface of the boss. In certain embodiments, the at least one channel 88 is positioned such that the proximal opening of the channel is adjacent to a radial edge of the boss 62. In additional embodiments, the channel 88 may be positioned further within an interior of the boss 62, such that the proximal opening of the channel is a non-nominal distance from the radial edge of the boss.

Embodiments of the present invention provide for the channel 88 to be cylindrical, such that the cutout in the distal-facing surface 80 is generally elliptical in shape along its longitudinal axis. In such an embodiment, a proximal most width of the channel is of generally the same size as a distal most width of the channel. In other embodiments, the channel may be teardrop-shaped, such that the cutout is generally shaped in the form of a tear drop or a cone along its longitudinal axis. In such an embodiment, a proximal most width of the channel is wider than a distal most width. The above-mentioned cutout shapes are provided for exemplary purposes only and are non-limiting. For instance, the cutouts may be in the shape of ovals, triangles, or the like. Embodiments of the present invention contemplate the use of one or more channels presenting cutouts of any shape that may facilitate the flow of fluid through the valve assembly 12. Variations of the cutout shape may be required based on specific requirements for a particular fluid and/or drug delivery, such as flow rates or viscosity characteristics. In addition, embodiments of the present invention may provide for more than one channel 88 to be included within the boss 62, as will be described in more detail below.

As best illustrated in FIG. 3, the luer lock fitting 14 is preferably a unitary fitting molded from a thermoplastic material, a synthetic resin, or the like. The fitting 14 includes a proximal annular valve cover 92, a distal annular inner barrel 94, and a distal annular outer connection wall 96. The fitting 14 also presents a proximal connection end 98 with proximal and distal axial surfaces 100,102, and proximal and distal shoulders 104,106 and is designed to be received by the distal socket of the valve support 16. The connection end 98 is designed to mate with the sidewall 60 so that respective surfaces 74,100, shoulders 78,104, and surfaces 76,102 engage one another to interconnect the fitting 14 and the valve support 16 and to secure the flow control valve 18, as will be discussed further. The annular base 26 of peripheral catheter 20 is threaded into the fitting 14, between the inner barrel 94 and outer connection wall 96. The fitting 14 also presents fluid passageway 48c that extends through the inner barrel 94 and valve cover 92. While the fitting 14 may be configured as a luer lock fitting, the principles of the present invention are equally applicable where fitting 14 includes a different type of connector for attachment to the catheter 20 (or for attachment to other infusion/aspiration set components such as a needle or tubing).

The valve cover 92 also presents a distal annular flange-engaging face 110 spaced radially between the proximal surface 100 and the passageway 48c, with the distal face 110 preferably including an endless annular groove 112 for receiving and holding the flow control valve 18 precisely between the valve support 16 and fitting 14. However, it is also within the scope of the present invention where the valve seat 58 is alternatively configured to receive the flow control valve 18, as will be discussed further.

Turning to FIG. 8, the flow control valve 18 is configured to selectively permit distal and proximal fluid flow through the valve assembly 12 and includes a peripheral flange 116 and a central body 118 surrounded by the flange 116. The body 118 and flange 116 are integrally formed from resilient silicone, but could include another synthetic resin material. In certain embodiments, the central body 118 may be arcuate-shaped, such as is illustrated in FIG. 8. In additional embodiments, the central body 118 may be substantially arcuate-shaped, such as hemispherical or parabolical. In still other embodiments, the central body 118 may include various other shapes, such as conical, cylindrical, rectangular, square, or the like. In even further embodiments, the central body 118 of the valve 18 may be complementary-shaped with a shape of at least portions of the boss 62. The body 118 comprises a wall 120 that may present proximal-facing and distal-facing surfaces 120a, 120b. In embodiments where the body 118 is arcuate-shaped, surfaces 120a, 120b may be concave and convex, respectively. The wall 120 also includes a distal end, and a thickness of the wall decreases progressively to the distal end of the wall. The body 118 also includes a rib 122 extending along the proximal-facing surface 120a of the wall 120. Yet further, the body 118 presents opposed interior valve edges 124 that extend perpendicularly relative to the rib 122 and extend axially through the body 118 to define a slit 126. In additional embodiments of the present invention, the edges 124 may extend inline, or parallel, relative to the rib 122 such that the slit 126 is similarly inline, or parallel, to the rib. In further embodiments, the body 118 may include a plurality of slits 126 that extend therethrough.

Embodiments of the present invention also provide for the slit 126, defined by the edges 124, to vary in length depending on a cracking pressure required for specific applications. In typical configurations, the slit 126 extends in opposite directions from the distal end of the valve 18 down the body 118 to approximately midway between the distal end and the flange 116. However, in applications that require a lower cracking pressure, such as an inline check valve system discussed in more detail below, the slit 126 may be relatively longer and extend down the body 118 further than approximately midway between the distal end and the flange 116. Such low cracking pressures may facilitate, for instance, the infusion of fluids and/or medications from fluid bags, drip chambers, or the like. Alternatively, in applications that require a higher cracking pressure, such as in Y-site check valve and manifold check valve systems discussed in more detail below, the slit 126 may be relatively shorter and extend down the body 118 less than approximately midway between the distal end and the flange 116. Such high cracking pressures may be appropriate, for instance, for the administration of fluids and/or medications from syringes or other injection devices. Regardless of whether the length of the slit 126 provides for a higher or a lower cracking pressure, embodiments of the present invention function to restrict fluid from flowing proximally through the valve assembly 12. Additional features of the body 118 are disclosed in U.S. Pat. No. 7,967,797, issued Jun. 8, 2011, entitled INTRAVASCULAR VALVE COMPONENT WITH IMPROVED VALVE POSITIONING, and U.S. Pat. No. 7,959,614, issued Jun. 14, 2011, entitled PRESSURE ACTUATED FLOW CONTROL VALVE, both of which are hereby incorporated by reference in their entirety.

The flange 116 includes an endless annular flange wall 128 surrounding and attached to the body 118 (see FIG. 8). The flange 116 also includes an endless annular valve-seating projection 130 extending distally from the flange wall 128 and spaced radially between an outermost edge 132 of the flange wall 128 and the body 118. Preferably, the projection 130 is spaced radially outwardly from the body 118 to permit the edges 124 to flex between open and closed configurations, as will be discussed. Embodiments of the present invention are also applicable where the projection 130 is alternatively configured to provide a mechanism for precisely seating the flow control valve 18 within the valve assembly 12 (see FIG. 3). For instance, the projection could extend proximally from the flange wall 128. Furthermore, multiple projections 130 could extend distally and/or proximally from the flange wall 128 to secure the flow control valve 18. For example, the projection 130 could comprise multiple arcuate segments that are spaced circumferentially from one another and cooperatively extend about the body 118. Alternatively, the projection 130 could include multiple radially-spaced segments.

The flow control valve 18 is assembled between the valve support 16 and fitting 14 by positioning the valve 18 on valve seat 58. In particular, the distal end of the wall 120 of the valve 18 is inserted into a proximal end of the passageway 48c, and the projection 130 is inserted into the annular groove 112. The projection 130 and groove 112 are preferably shaped to guide the flow control valve 18 into axial alignment with the fitting 14. Preferably, the groove 112 and projection 130 are complementally shaped so that the projection 130 fits snugly within the groove 112 and the flow control valve 18 is coaxially aligned with the fitting 14 (thereby positioning the central body 118 concentrically within the passageway 48c). In this manner, the interengagement between the groove 112 and projection 130 restricts relative radial movement between the flow control valve 18, support body 22, and fitting 14. In addition, the groove 112 and projection 130 permit the flow control valve 18 to be selectively angularly rotated about the valve axis and relative to the support body 22 and fitting 14, although this is likely unnecessary with the illustrated embodiment because of the symmetrical construction of the control valve 18.

The following descriptions of the positioning of the valve 18 are applicable when the valve is in a natural or an at rest state (i.e., fluid is not flowing in either a proximal or distal direction through the valve assembly 12). The flow control valve 18 is positioned onto the valve seat 58 and over the boss 62 by locating a proximal surface of the flange wall 128 against the flange-engaging face 72. The valve 18 is positioned over the boss 62, such that at least a portion of the distal end 84 of the boss 62 may contact the valve 18. In certain embodiments of the present invention, at least a portion of the distal end 84 contacts at least a portion of the rib 122 that extends along the proximal-facing surface 120a of the valve 18. In additional embodiments, and as discussed above, a portion of the distal end 84 of the boss 62 may be flat instead of convex (see FIGS. 6-7). In such an embodiment, at least a portion of the flat surface 86 of the boss contacts the valve 18. And in certain embodiments, at least a portion of the flat surface 86 of the boss may contact the rib 122 of the valve 18. Although at least a portion of the boss 62 contacts at least a portion of the valve 18, a radial diameter of the boss is generally smaller than a radial diameter of the proximal-facing surface 120a of the valve 18. Thus, except for the at least a portion of the boss 62 that contacts the valve 18, the remaining surface area of the boss generally does not contact the valve 18. Such structure and relative positioning between the boss 62 and the valve 18 leaves a space, hereinafter a fluidic chamber 134, that collects the fluid and/or medication that is introduced into the valve assembly 12 as it passes through the one or more channels 88 of the boss. As fluid builds up in the fluidic chamber 134, the fluid creates a pressure that can be used to open the valve slit 126 to let the fluid through the valve 18, as will be discussed in more detail below.

As discussed previously, the fitting 14 is secured to the valve support 16 by inserting the connection end 98 into the distal socket of the valve support. The valve support 16 and fitting 14 are further secured by attaching respective adjacent pairs of surfaces using a conventional ultrasonic welding process to form an hermetic seal between the valve support 16 and fitting 14. Embodiments of the present invention are also applicable where the valve support and fitting are alternatively attached to one another, e.g., where the valve support 16 and fitting 14 are attached by a snap-fit interengagement or adhered to one another using a suitable adhesive.

With the connection end 98 inserted, the valve support 16 and fitting 14 cooperatively present an internal valve chamber that receives the flow control valve 18. The faces 72,110 engage the flange wall 128 on corresponding sides and compress the flange wall 128 into a compressed state so as to firmly hold the valve 18 within the valve assembly 12. More preferably, the valve support 16 and fitting 14 are interconnected so that a thickness dimension T (see FIG. 8) of the flange wall 128 is axially compressed from an uncompressed state to the compressed state by an amount that ranges from about 0.003 inches to about 0.008 inches. Most preferably, the amount of compression of the thickness dimension T between uncompressed and compressed states is about 0.005 inches. This configuration provides a slight clearance between the flange wall 128 and valve support 16. As a result, the illustrated flow control valve 18 can be precisely coaxially aligned with the valve support 16, fitting 14, and passageways 48*a*, 48*b*, 48*c*, and the flange wall 128 can be compressed between the valve support 16 and fitting 14 while permitting the body 118 to flex normally to allow distal fluid flow.

Turning again to FIGS. 1-3, the valve 18 is preferably designed to prevent fluid flow in the proximal direction. More particularly, the valve 18 prevents proximal flow regardless of the back-pressure (i.e., the relative pressure differential experienced by the distal-facing surface 120*b* of the wall 120 with respect to the pressure against the proximal-facing surface 120*a* of the wall) across the valve 18. In general, the back-pressure experienced by the valve 18 may correspond to a typical venous pressure of the patient. In certain circumstances (such as when drawing off fluids or when changing connectors or valve assembly components), the corresponding back-pressure may be higher than the typical venous pressure and could cause prior art valves to allow a proximal fluid flow. However, embodiments of the present invention prevent proximal fluid flow by utilizing the axially-extending boss 62 positioned proximally from the valve. As back-pressure increases, the pressure against the distal-facing surface 120*b* of the wall 120 forces the wall in a proximal direction, thus compressing the valve 18, or at least a portion of the valve 18, against the boss 62. Such a compression functions to compress the interior valve edges 124 together and against the boss 62, thus sealing the valve 18 closed and preventing any fluid from traveling in the proximal direction.

In addition, in prior art valves, if the back-pressure exceeds a threshold amount, the pressure could cause the valve to mechanically invert, such that a distal end of the valve is forced proximally from its natural position. Such a mechanical inversion could cause the slit 126 of the valve 18 to remain open and permit unobstructed fluid flow in the proximal direction. Embodiments of the present invention prevent such mechanical inversion by use of the boss 62 acting as a backstop for the valve 18. For instance, with typical venous pressures (e.g., between about 0.3 psi to about 0.7 psi) being applied to the distal-facing surface 120*b* of the wall 120, the boss 62 prevents mechanical inversion, and the slit 126 of the valve 18 remains in a closed and sealed position. In addition, embodiments of the present invention may provide for the boss 62 to prevent a mechanical inversion of the valve 18 and a corresponding fluid flow in the proximal direction in response to extreme back-pressures, i.e., up to about 100 psi being applied to the distal-facing surface 120*b*.

As best illustrated in FIG. 3, the valve 18 is also preferably designed to selectively prevent fluid flow in the distal direction when the valve is in the closed configuration. The valve 18 prevents distal fluid flow when a forward-pressure (i.e., the relative pressure differential experienced by the proximal-facing surface 120*a* of the wall 120 with respect to the pressure against the distal-facing surface 120*b* of the wall) across the valve 18 is below a predetermined cracking pressure. When a forward-pressure is applied to the proximal-facing side 120*a* of the valve 18 (e.g., by injecting fluid or medication from a fluid supply) and such forward-pressure exceeds the cracking pressure, the valve 18 opens into an open configuration (where the interior valve edges 124 are shifted distally and away from each other) to allow fluid to flow distally through passageway 48*b* and into passageway 48*c*. Embodiments of the present invention provide for the cracking pressure to be relatively low, thus corresponding to a low cracking pressure. In particular, the size, shape, and materials used in the manufacture of the flow control valve 18 naturally facilitate a low cracking pressure. In addition, the fluidic chamber 134 provides a natural cavity for the fluid to collect, wherefrom the fluid acts against the proximal-facing surface 120*a* of the valve 18. The fluid pressure on the proximal-facing surface 120*a* works to assist in opening the valve, thus enhancing the low cracking pressure of the valve.

In operation, the valve assembly 12 permits distal fluid flow from the fluid source (not shown) to the peripheral catheter 20 when the front-pressure exceeds the cracking pressure. Thus, the fluid from the injection source travels through the passageway 48*b* of the valve support 16 and through the one or more channels 88 in the boss 62 and collects in the fluidic chamber 134. The fluid begins to build up pressure against the proximal-facing surface 120*a* of the valve 18 as it collects in the fluidic chamber. Once the pressure in the fluidic chamber exceeds the cracking pressure, the interior valve edges 124 are shifted in the distal direction and at least partly away from each other to open the slit 126 and allow fluid to pass from the passageway 48*b* to the distal passageway 48*c*. As discussed above, embodiments of the present invention provide for the slit 126 to vary in length to affect the cracking pressure necessary to open the valve and to allow fluid to flow in the distal direction. Thus, slit 126 with a relatively longer length will have a lower cracking pressure, such that the pressure necessary to open the valve 18 to allow a distal fluid flow will be less. Conversely, slit 126 with a relatively shorter length will have a higher cracking pressure, such that the pressure necessary to open the valve 18 will be greater.

As previously discussed, the valve assembly 12 can be used in other applications or with other types of connection components, tubing, etc. For instance, as illustrated in FIGS. 9-13, a variant of the valve assembly 12 may be used as part of an inline check-valve system 138. In inline system 138, inline valve assembly 140 is positioned inline between distal and proximal tubular members 142,144. The inline valve assembly 140 is structurally similar in all respects to the valve assembly 12, except that valve assembly 140 includes luer slip locks as opposed to luer locks on its distal and proximal ends. Specifically, instead of using the luer lock fitting 14, the valve assembly 140 includes a slip luer fitting 146 on its distal end. The slip luer fitting 146 is structurally similar in all respects to the luer lock fitting 14, except that the luer lock mating parts of fitting 14 are replaced with a distal annular inner barrel 150 and a distal annular outer connection wall 152. Similarly, instead of using the valve support 16, the valve assembly 140 includes a luer slip valve support 148 on its proximal end. The slip luer valve support 148 is structurally similar in all respects to the valve support 16, except that the luer lock mating parts of valve support 16 are replaced with proximal annular inner barrels 154 and proximal outer connection walls 156. The barrels 150,154 and walls 152,156 of the slip luer lock fitting 146 and the slip luer valve support 148 are sized such that the tubular members 142,144 may be attached to the fittings and valve support by inserting the tubular members between the barrels and the outer walls. The outer walls 152,156 may be positioned at such a distance from the barrels 150,154 that the tubular members 142,144 are securely held in place by the compression of the outer walls and the barrels. In such an embodiment, fluid may be delivered from the tubing that connects the inline support assembly and will flow through the valve assembly 140 as was described in previous embodiments for valve assembly 12. After the fluid has passed through the valve assembly 140, it continues on through the tubing that connects to the distal end of the valve assembly. As can be appreciated, the inline check-valve system 138 only allows fluid to flow in the direction permitted by the flow control valve, i.e. from proximal end to distal end. Such restriction is caused by the boss 62 functioning to prevent the backflow of fluids in a proximal direction into the fluid source or otherwise upstream when infusing fluids or medication downstream.

Figure 14:
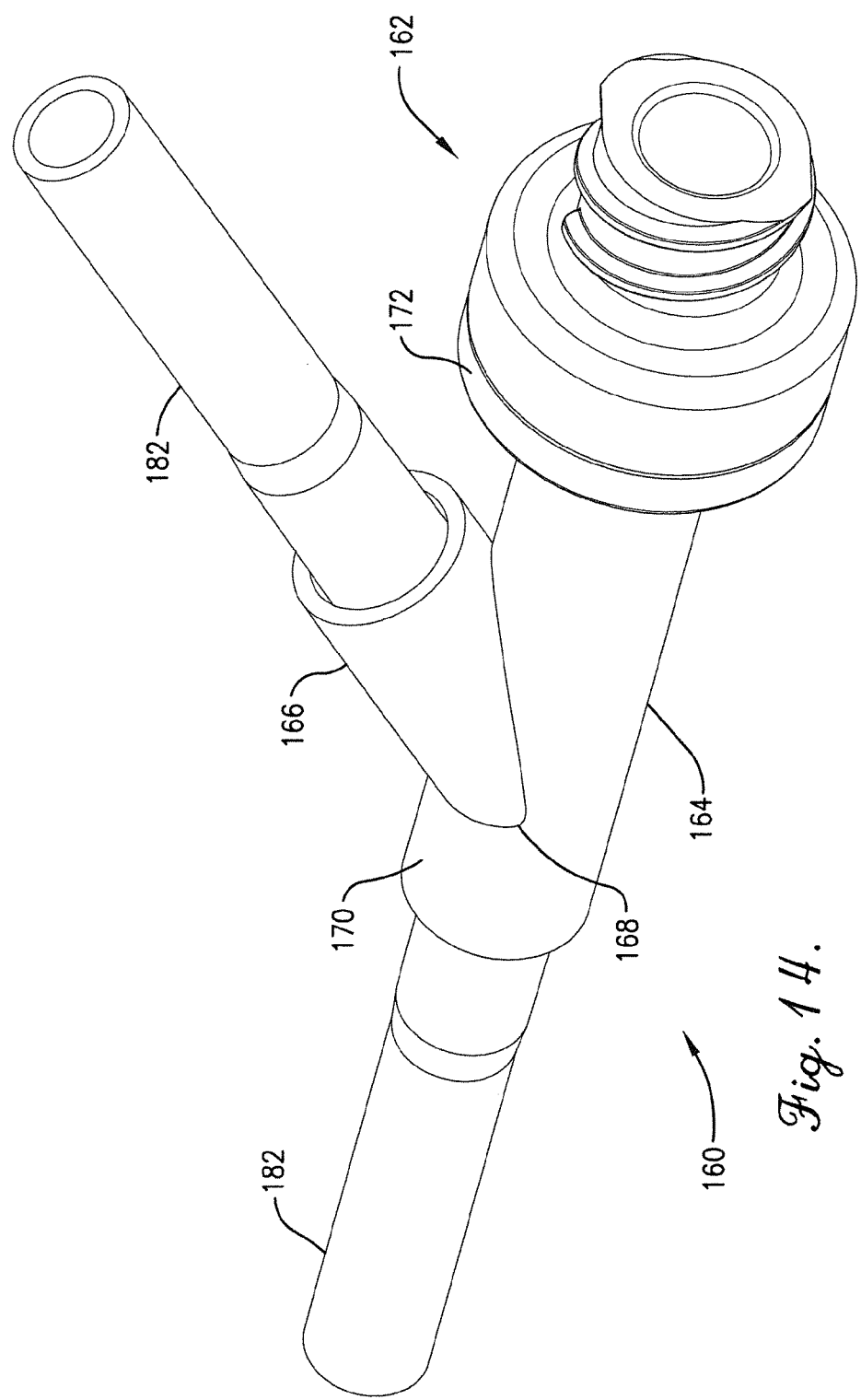
FIG. 14 is a perspective view of a Y-site check valve system embodiment of the present invention, including a Y-site check valve assembly.
Figure 15:
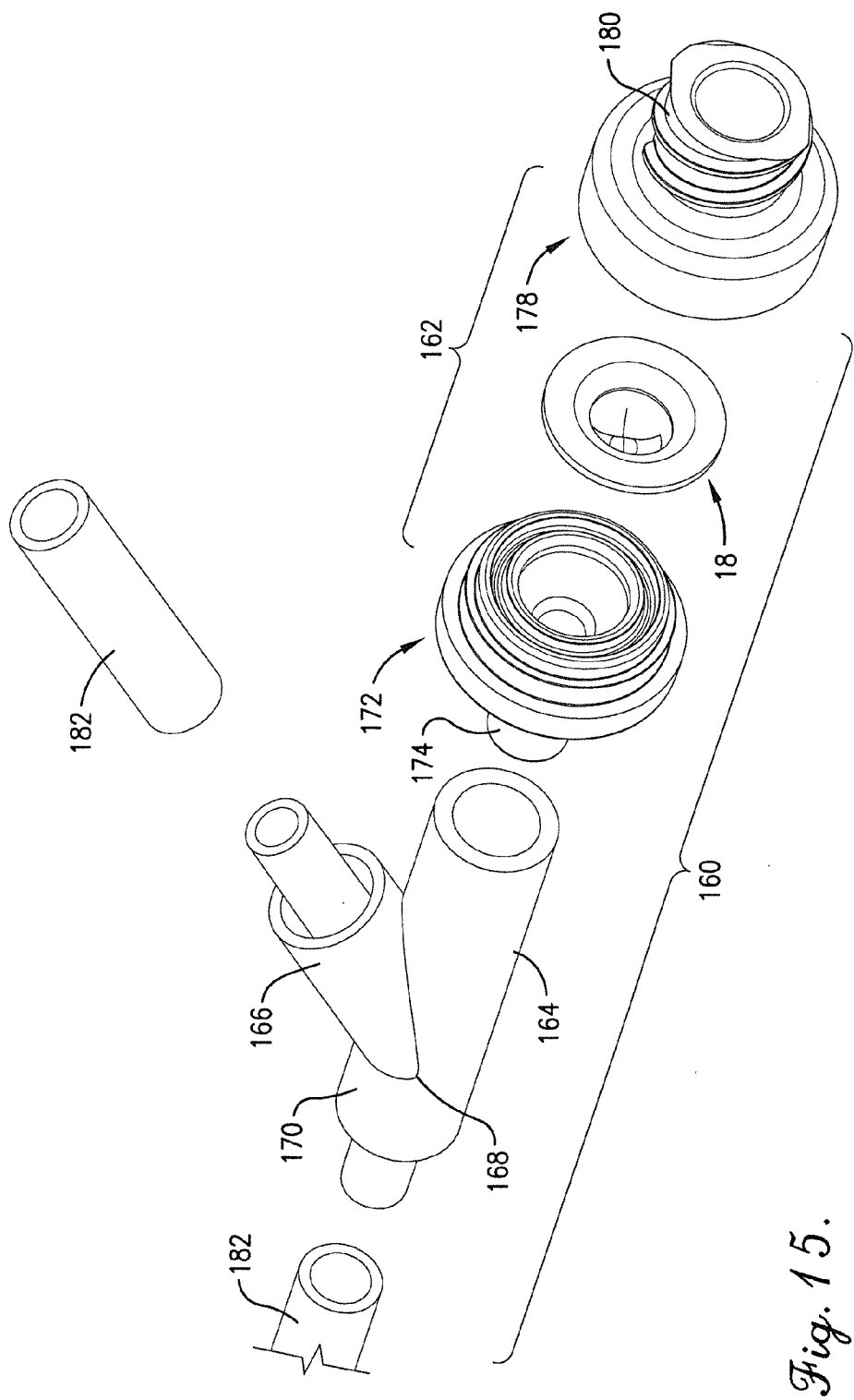
FIG. 15 is an exploded proximal perspective view of the Y-site check valve system shown in FIG. 14, including the Y-site check valve assembly and particularly showing a first leg, a second leg, a joint, a single base leg, a slip luer fitting, a flow control valve, and a valve support.
Figure 16:
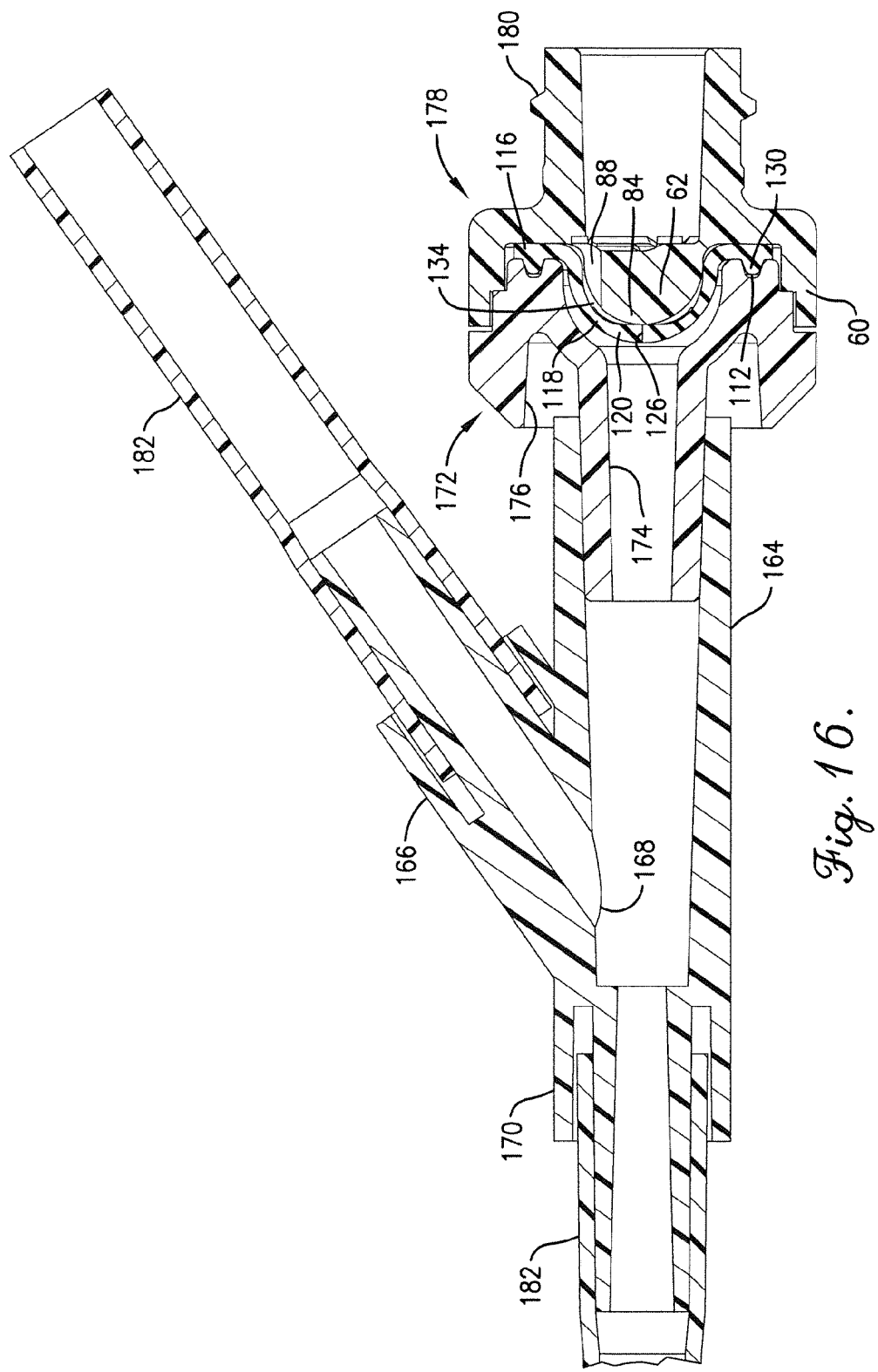
FIG. 16 is a cross section of the Y-site check valve system shown in FIGS. 14-15, including the Y-site check valve assembly and particularly showing tubular members, a slip luer fitting, a flow control valve, and a slip luer valve support.

As illustrated in FIGS. 14-16, embodiments of the present invention additionally provide for a variant of the valve assembly 12 to be used in a Y-site check valve system 160. In such an embodiment Y-site check valve assembly 162 is positioned at the proximal end of a first leg 164 of the Y-site system 160. The Y-site system 160 includes a second leg 166 that joins the first leg 164 at a joint 168 that is some distal distance from the valve assembly 162. The Y-site system 160 further includes a single base leg 170 that is attached distally to the joint 168. The Y-site valve assembly 162 is structurally similar in all respects to valve assembly 12 except that the luer lock fitting 16 is replaced with a slip luer fitting 172. In addition, the slip luer fitting 172 is structurally similar in all respects to the luer lock fitting 14 with the exception that the luer lock mating parts of fitting 14 are replaced with a distal annular inner barrel 174 and a distal outer connection wall 176. In certain embodiments, the slip luer fitting 172 may be identical to slip luer fitting 146 from the inline check valve system 138. In additional embodiments, the wall 176 of slip luer fitting 172 may be substantially shorter than the wall 152 from the slip luer fitting 146. However, either embodiment provides for a proximal end of the first leg 164 to fit onto the slip luer fitting 172 by being positioned over the fitting's inner barrel 174. A solvent may be applied to the proximal end of the first leg 164 and the inner barrel 174 to secure the first leg and the inner barrel together. In certain embodiments, the Y-site check valve system 160 includes a valve support 178 with a luer lock connection 180, with the valve support 178 similar in all respects to the valve support 16 described above. Once each of the above-described components are connected, the Y-site system 160 facilitates further attachments and connections to be attached to the luer lock connection 180 of the valve support 178. In addition, a free end of the second leg 166 and a free end of the single base leg may include slip luer fittings, such that tubular members 182 may be inserted onto each of the free ends. The Y-site valve assembly 162 permits fluids and medication to pass through the first leg 164 of the valve system 160 and to mix and combine with the fluids and/or medication flowing through the second leg 166 at the joint 168 of the valve system. In addition, the Y-site valve assembly 162 prevents for reflux of the fluid, such that incompatible fluids will not be intermixed beyond any proximal distance from the valve of the valve assembly.

Figure 17:
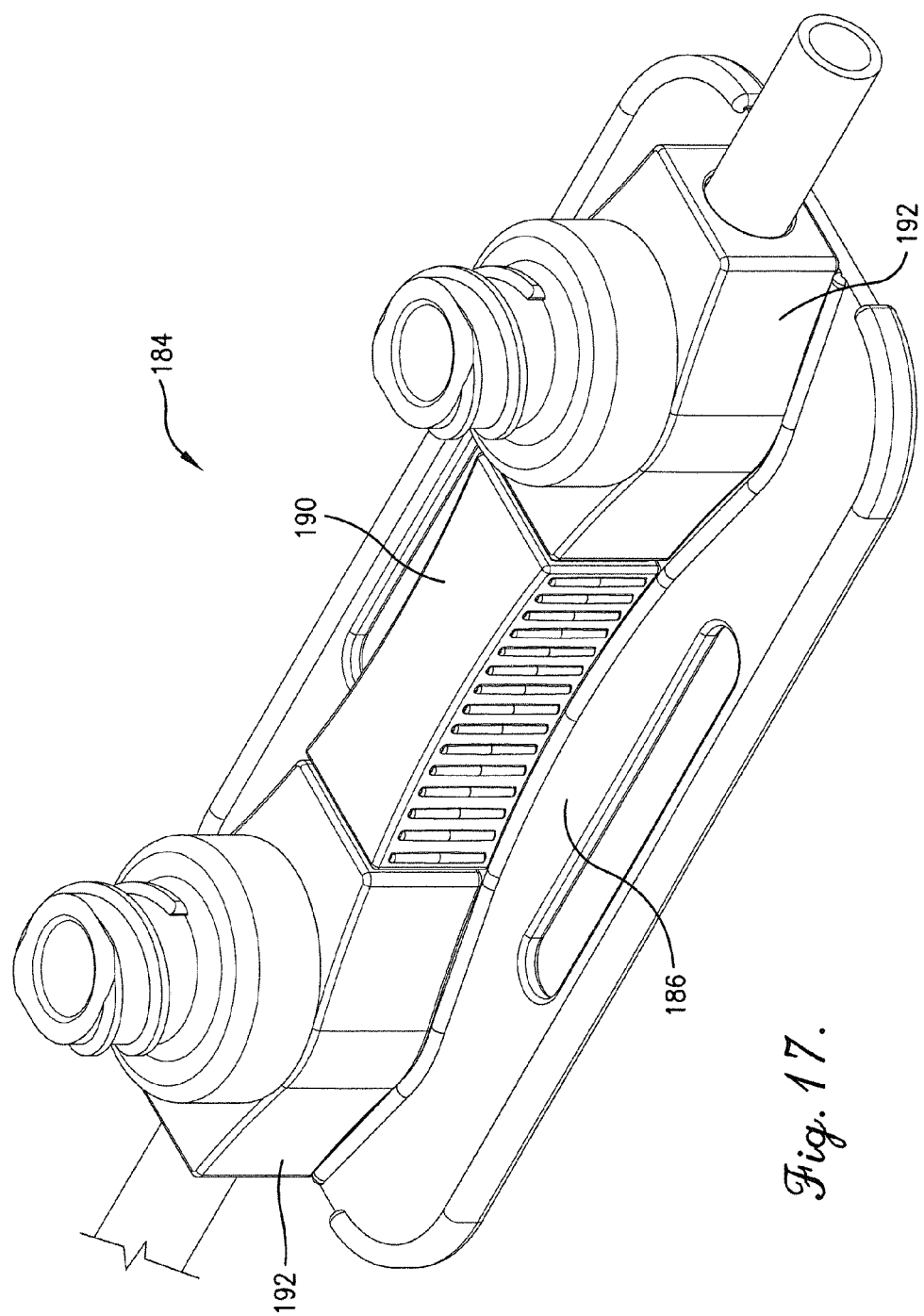
FIG. 17 is a perspective view of a manifold check valve system embodiment of the present invention, including two manifold check valve assemblies.
Figure 18:
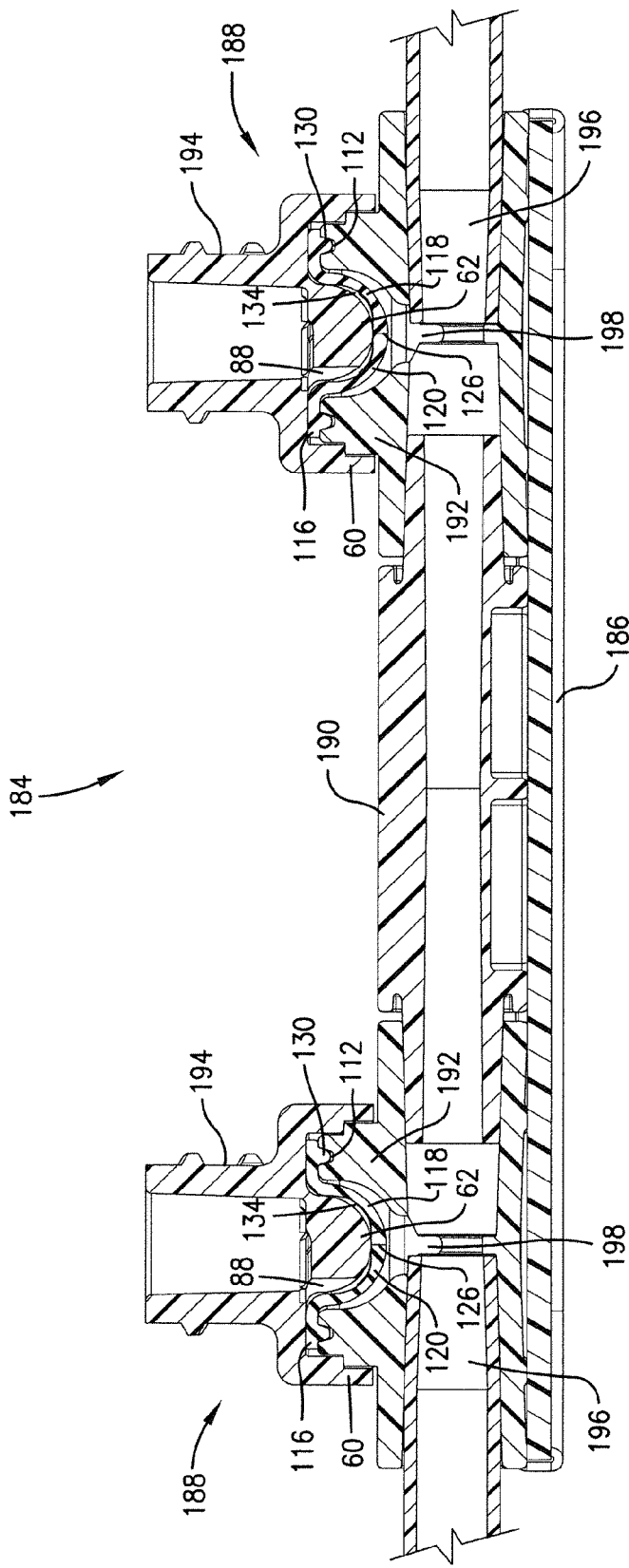
FIG. 18 is a cross section of the manifold check valve system shown in FIG. 17, showing a base module, the two manifold check valve assemblies, and a barrel-shaped interconnect.
Figure 19:
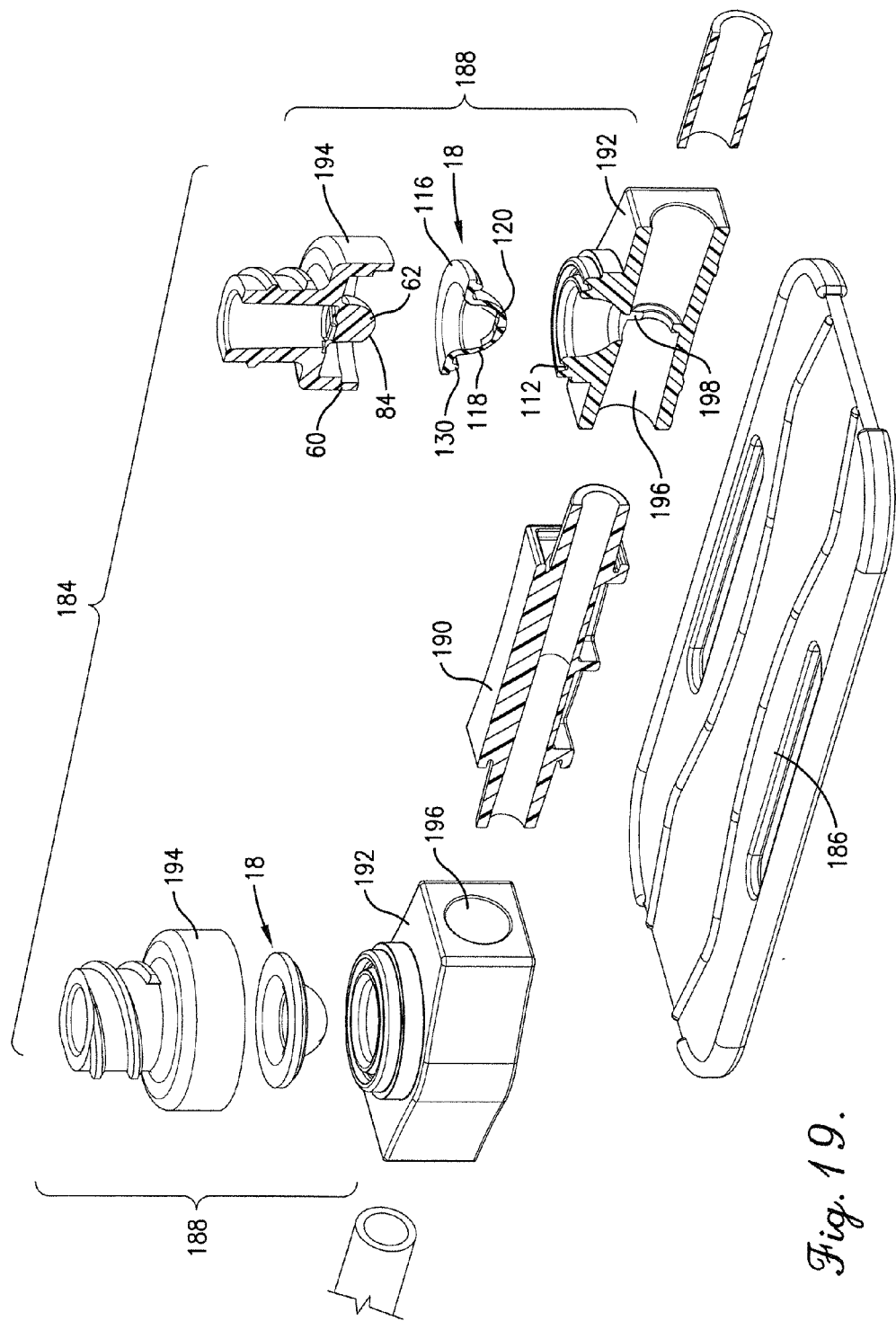
FIG. 19 is an exploded view of the manifold check valve system shown in FIGS. 17-18, particularly showing the base module, the two manifold check valve assemblies, and the barrel-shaped interconnect.

As illustrated in FIGS. 17-19, embodiments of the present invention additionally provide for a variant of the valve assembly 12 to be used in a manifold check valve system 184. The manifold check valve system 184 is comprised of a base module 186, two or more manifold check valve assemblies 188 secured to the base, and a barrel-shaped interconnect 190 that fluidly connects the valve assemblies 188. The base 186 may be constructed of any suitable medical grade material, such as, for example, polyethylene, polyvinyl chloride, Teflon, or mixtures thereof. The base provides a secure support for the valve assemblies 188 and interconnect 190. The interconnect 190 may similarly be made of polyethylene, polyvinyl chloride, Teflon, or mixtures thereof; however, in certain embodiments, the interconnect may simply be a section of silicone elastomer or polyurethane tubing. The valve assemblies 188 are structurally similar in all respects to the valve assembly 12 except that in place of luer lock fitting 14, the valve assemblies 188 include a manifold fitting 192 on distal ends of the valve assemblies 188. The manifold fitting 192 functions similar to the luer lock fitting 14 and slip luer fittings 146,172, in that it receives the flow control valve 18 and secures the valve in place against the valve support 194. However, the manifold fitting does not include a connector on its distal end. Instead, the manifold fitting 192 includes a tubular passageway 196 positioned perpendicularly to the direction of fluid flow through the valve assemblies 188. The manifold assemblies 188 include openings 198 that fluidly connect the flow control valve 18 to the tubular passageway 196. Thus, as fluid or medication flow distally through the manifold valve assemblies 188, they pass through the flow control valve 18 and on into the tubular passageway 196. Such an embodiment provides for a plurality of fluids and medications to be introduced from each of the valve assemblies 188 and to be intermixed within the tubular passageway 196. As with all embodiments of the present invention, the valve 18 and the boss 62 of the valve assemblies 188 prevent fluid from backflowing from the tubular passageway 196 back through the valve assemblies 188 in a proximal direction past the flow control valve 18. In additional embodiments, the manifold check valve system 184 may include a plurality of valve assemblies 188 connected in series, such that multiple sources of fluid or medications can be introduced and mixed without concern for intermixing of the fluids or medications in a proximal direction past the manifold valve assemblies 188.

In certain embodiments, the components of the manifold check valve system 184 may fit together in a modular design. Such a modular design facilitates a functional fit of the components, while permitting exterior portions of the components to form continuous connections. For instance, as illustrated in FIG. 17, exterior portions of the manifold fittings 192 connect in a continuous manner with exterior portions of the interconnect 190, such that although the fittings and manifold are separate components, they fit together to give an appearance of a single continuous component. Embodiments of the present invention provide for various check valve components to fit together in such modular design.

As can be appreciated, embodiments of the present invention contemplate the use of various mixing and matching of embodiments of the present invention as may be required. As a non-limiting example, an inline check valve assembly 140 may be attached to an end of the manifold system 184 inline with the tubular passageway 196. Such an embodiment would function similar to the manifold application described above; however, the inline check valve 140 would only facilitate the flow of fluid in a single direction through the manifold, thereby restricting reflux past the flow control valve and into the manifold. Such an embodiment would further reduce the concern for the unwanted reflux and intermixing of fluids or medications within the manifold.

The embodiments of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An intravascular check valve assembly to control fluid flow through the assembly in opposite distal and proximal directions, said valve assembly comprising:
   a valve case including attached proximal and distal case portions,
   said case portions presenting respective spaced apart fluid ports and a fluid passageway extending between the ports; and
   a flexible pressure-actuated flow control valve disposed along the fluid passageway to control fluid flow therethrough,
   said valve including a valve wall having a slit at a distal end of the wall,
   said valve wall presenting distal-facing and proximal-facing surfaces,
   said proximal case portion of the valve case including an axially-extending boss that distally projects from the proximal case,
   said axially-extending boss having an exterior surface and a distal end, wherein said exterior surface at said distal end of the boss terminates at a closed-ended apex to present a closed surface for contacting a portion of the proximal-facing surface of the valve wall, wherein said closed surface prevents said valve from flexing to open the slit in the proximal direction upon the closed surface contacting said portion of the proximal-facing surface of the valve wall,
   said axially-extending boss including one or more channels positioned adjacent to a radial-most edge of the boss, wherein the channels fluidly connect the fluid port of the proximal case to the proximal-facing surface of the valve wall,
   said valve wall flexing to open the slit in response to a fluid flowing in a distal direction through the channels,
   said valve wall compressing against the boss and closing the slit in response to fluid flowing in a proximal direction, thereby preventing fluid flow through the valve assembly in the proximal direction.

2. The intravascular check valve assembly as claimed in claim 1, wherein the axially-extending boss is generally hemispherical in shape.

3. The intravascular check valve assembly as claimed in claim 1, wherein said closed-ended apex of the axially-extending boss is flat, thereby presenting a distal-facing surface that is orthogonal to the valve assembly's axial direction.

4. The intravascular check valve assembly as claimed in claim 1, wherein the one or more channels of the axially-extending boss includes three channels equally spaced around the radial-most edge of said boss.

5. The intravascular check valve assembly as claimed in claim 1, wherein longitudinal axes of the one or more channels of the axially-extending boss are generally parallel with a longitudinal axis of the check valve assembly.

6. The intravascular check valve assembly as claimed in claim 1, wherein the one or more channels of the axially-extending boss have a generally cylindrical shape, such that a proximal most width of the channels are of generally the same size as a distal most width.

7. The intravascular check valve assembly as claimed in claim 1, wherein the one or more channels of the axially-extending boss have a generally tear drop shape, such that a proximal most width of the channels are wider than a distal most width.

8. An intravascular check valve assembly to control fluid flow through the assembly in opposite distal and proximal directions, said valve assembly comprising:
   a valve case including attached proximal and distal case portions,
   said case portions presenting respective spaced apart fluid ports and a fluid passageway extending between the ports; and
   a flexible pressure-actuated flow control valve disposed along the fluid passageway to control fluid flow therethrough,
   said valve including a central valve wall having a slit at a distal end of the wall,
   said valve wall presenting distal-facing and proximal-facing surfaces,
   said proximal case portion of the valve case including an axially-extending boss that distally projects from the proximal case,
   said axially-extending boss having an exterior surface and a distal end, wherein said exterior surface at said distal end of the boss terminates at a closed-ended apex to present a closed surface for contacting a portion of the proximal-facing surface of the valve wall, wherein said closed surface prevents said valve from flexing to open the slit in the proximal direction upon the closed surface contacting said portion of the proximal-facing surface of the valve wall,
   said axially-extending boss including one or more channels positioned adjacent to a radial-most edge of the boss, wherein the channels fluidly connect the fluid port of the proximal case to the proximal-facing surface of the valve wall,
   wherein a proximal most edge of the proximal-facing surface of the valve wall presents a circular ring, and the proximal most surface of the axially-extending boss presents a generally circular surface,
   wherein a radius of the circular ring is larger than a radius of the circular surface, such that except for the portion of the distal end of the boss that contacts the proximal-facing surface of the valve, a fluidic chamber exists between the boss and the proximal-facing surface,
   said valve wall flexing to open the slit in response to a fluid flowing in a distal direction through the channels and into the fluidic chamber between the boss and the proximal-facing surface,
   said valve wall compressing against the boss and closing the slit in response to fluid flowing in a proximal direction, thereby preventing fluid flow through the valve assembly in the proximal direction.

9. The intravascular check valve assembly as claimed in claim 8, wherein the axially-extending boss is generally hemispherical in shape.

10. The intravascular check valve assembly as claimed in claim 8, wherein said closed-ended apex of the axially-extending boss is flat, thereby presenting a distal-facing surface that is orthogonal to the valve assembly's axial direction.

11. The intravascular check valve assembly as claimed in claim 8, wherein the one or more channels of the axially-extending boss includes three channels equally spaced around the radial-most edge of said boss.

12. The intravascular check valve assembly as claimed in claim 8, wherein longitudinal axes of the one or more channels of the axially-extending boss are generally parallel with a longitudinal axis of the check valve assembly.

13. The intravascular check valve assembly as claimed in claim 8, wherein the one or more channels of the axially-extending boss have a generally cylindrical shape, such that a proximal most width of the channels are of generally the same size as a distal most width.

14. The intravascular check valve assembly as claimed in claim 8, wherein the one or more channels of the axially-extending boss have a generally tear drop shape, such that a proximal most width of the channels are wider than a distal most width.

\* \* \* \* \*